United States Patent
Matesevac et al.

[11] Patent Number: 6,117,418
[45] Date of Patent: Sep. 12, 2000

[54] STICK COMPOSITIONS

[75] Inventors: Ronald Matesevac, Teaneck; Jeffrey S. Graf, Ridgewood; Philip Franco, Ocean Grove, all of N.J.

[73] Assignee: Avon Products, Inc., New York, N.Y.

[21] Appl. No.: 09/228,363

[22] Filed: Jan. 11, 1999

Related U.S. Application Data

[63] Continuation-in-part of application No. 08/949,219, Oct. 10, 1997, Pat. No. 5,858,336.

[51] Int. Cl.[7] ............................... A61K 7/32; A61K 7/00
[52] U.S. Cl. ..................... 424/65; 424/78.02; 424/78.08; 424/78.18; 424/401
[58] Field of Search .................... 424/65, 78.02, 424/78.08, 78.18, 401

[56] References Cited

U.S. PATENT DOCUMENTS

| | | | |
|---|---|---|---|
| 4,822,602 | 4/1989 | Sabatelli | 424/65 |
| 4,906,454 | 3/1990 | Melanson, Jr. et al. | 424/47 |
| 4,944,937 | 7/1990 | McCall | 424/65 |
| 4,970,220 | 11/1990 | Chaussee | 514/358 |
| 5,114,717 | 5/1992 | Kuznitz et al. | 424/401 |
| 5,120,541 | 6/1992 | Macaulay et al. | 424/401 |
| 5,128,123 | 7/1992 | Brewster et al. | 424/65 |
| 5,182,103 | 1/1993 | Nakane | 424/78.03 |
| 5,198,218 | 3/1993 | Kuznitz et al. | 424/401 |
| 5,270,034 | 12/1993 | Cheng | 424/68 |
| 5,284,649 | 2/1994 | Juneja | 424/67 |
| 5,316,761 | 5/1994 | Brazinsky | 424/65 |
| 5,368,848 | 11/1994 | Brazinsky et al. | 424/65 |
| 5,376,363 | 12/1994 | Benfatto et al. | 424/66 |
| 5,378,468 | 1/1995 | Suffis et al. | 424/401 |
| 5,405,605 | 4/1995 | Shin | 424/68 |
| 5,407,668 | 4/1995 | Kellner | 424/65 |
| 5,417,876 | 5/1995 | Tokosh et al. | 252/108 |
| 5,417,962 | 5/1995 | Brodowski et al. | 424/65 |
| 5,424,070 | 6/1995 | Kasat et al. | 424/401 |
| 5,458,880 | 10/1995 | Kasat et al. | 424/401 |
| 5,462,736 | 10/1995 | Rech et al. | 424/401 |
| 5,474,778 | 12/1995 | Ichikawa et al. | 424/401 |
| 5,484,597 | 1/1996 | Slavtcheff et al. | 424/401 |
| 5,520,907 | 5/1996 | Orofino et al. | 424/65 |
| 5,603,925 | 2/1997 | Ross et al. | 424/65 |
| 5,626,852 | 5/1997 | Stuffis et al. | 424/401 |
| 5,639,463 | 6/1997 | Kilpatrick-Liverman et al. | 424/401 |

OTHER PUBLICATIONS

Harry's Cosmeticology, Wilkinson et al., eds., Seventh edition, 1982, pp. 139–140.

*Primary Examiner*—John Kight
*Assistant Examiner*—Charanjit S. Aulakh
*Attorney, Agent, or Firm*—Ohlandt, Greeley, Ruggiero & Perle, L.L.P.

[57] ABSTRACT

A clear stick composition is disclosed that includes a solvent, a gelling agent, a plasticizing/solubilizing agent and a clarity/stability agent. The clarity/stability enhancing agent is preferably polyoxypropylene (10) butanediol (PPG-10 butanediol).

20 Claims, No Drawings

STICK COMPOSITIONS

RELATED APPLICATION

This application is a continuation-in-part of U.S. patent application Ser. No. 08/949,219, filed Oct. 10, 1997, now U.S. Pat. No. 5,858,336, Jan. 12, 1999.

FIELD OF THE INVENTION

The present invention relates generally to a stick composition. More particularly, this invention relates to a stick composition that exhibits improved transparency and translucency, and demonstrates improved stability, especially with respect to syneresis and maintenance of transparency/translucency. The present invention also provides an improved clear stick composition that can be used to deliver topically deodorants and fragrances.

BACKGROUND OF THE INVENTION

Stick compositions are often used as topical delivery vehicles in the cosmetic and pharmaceutical industries. For example, stick compositions may be used to deliver ingredients such as deodorants/antiperspirants and fragrances. In particular, it has been discovered that stick deodorants and/or antiperspirants that are clear or translucent (instead of opaque) are preferred by many consumers.

However, many clear stick compositions suffer from certain limitations. Some compositions are unstable over time or under the extremes of temperature encountered during shipment and storage. Others cause an unpleasant stinging sensation when they are applied to sensitive skin areas, such as the underarm area. Some such compositions produce sticks that are very hard, and do not have adequate payoff on the skin. Accordingly, a demand exists for a stick composition that has improved transparency/translucency and improved stability, any also has a smooth, silky feel on contact with skin.

SUMMARY OF THE INVENTION

It is an object of the present invention to provide a clear stick deodorant that has improved clarity and improved stability.

It is another object of the present invention to provide such a clear stick composition that is stable over time and under a wide range of temperatures.

It is a further object of the present invention to provide such a clear stick composition that is economical to manufacture.

It is a still further object of the present invention to provide such a clear stick composition that does not sting when applied to skin.

To the accomplishment of the foregoing objects and advantages, the present invention, in brief summary, is a stick composition including a solvent, a gelling agent, a plasticizing/solubilizing agent, and a clarity/stability enhancing agent. Preferably, the clarity/stability enhancing agent is PPG-10 butanediol.

DETAILED DESCRIPTION OF THE INVENTION

The stick composition of the present invention provides a solid mass that is rigid enough to maintain its shape as a stick, but that is soft enough to provide good payoff of the product as well as deliver the active ingredient or ingredients to the skin. In addition, the stick composition is stable over time and under extreme temperature conditions, especially those temperature conditions encountered during shipping and storage. The stick composition of the present invention resists syneresis better than most conventional stick compositions. The terms "stick composition(s)" and "clear stick composition(s)" are used interchangeably herein.

Stick compositions according to the present invention include a solvent, a gelling agent, a plasticizing/solubilizing agent (hereinafter referred to as "plasticizer(s)") and a clarity/stability enhancing agent.

The solvent is preferably a $C_2$ to $C_6$ polyhydric alcohol, water, or a combination thereof. The polyhydric alcohol serves also as an emollient. Preferably, the polyhydric alcohol is propylene glycol. Most preferably, the solvent is a mixture of water and propylene glycol. The solvent is preferably present at about 70 to about 95 weight percent (wt %), with a range from about 70 to about 90 wt % being more preferred. When the solvent includes water, the stick composition preferably has from about 10 to about 20 wt % water. All weight percentages (wt %) disclosed herein are based upon the total weight of the stick composition unless otherwise stated.

The stick composition of the present invention includes a gelling agent. The gelling agent is preferably present at about 4 to about 10 wt %, with a range from about 5 to about 8 wt % being preferred. The gelling agent is preferably a soap-type gelling agent. More preferably, the gelling agent is a mixture of sodium salts of different fatty acids (hereinafter "sodium salt fatty acid mixture"). Most preferably, the sodium salt fatty acid mixture includes sodium stearate.

It is also preferred that the sodium stearate is a mixture of two or more commercially available grades of sodium stearate (hereinafter "sodium stearate mixture"). When the gelling agent is the sodium stearate mixture, it is preferred that the stick composition has up to about 8 wt % of the sodium stearate mixture. For enhanced stability, the sodium stearate mixture preferably is a mixture of two commercial grades of sodium stearate, hereinafter "sodium stearate grade 1" and "sodium stearate grade 2", respectively. The sodium stearate grade 1 preferably contains from about 30% to about 41% $C_{20}$ and higher saturated chain length fatty acids. The most preferred sodium stearate grade 1 is sodium stearate (OP-200) sold by RTD Chemicals. The sodium stearate grade 2 preferably contains more than about 88% $C_{16}$ and $C_{18}$ fatty acids, and up to about 2% fatty acids longer than $C_{18}$. The most preferred sodium stearate grade 2, is sodium stearate C-1 sold by Witco. This preferred sodium stearate mixture provides a superior balance of acceptable product odor, transparency and syneresis resistance. Tables A and B, below, set forth the preferred fatty acid distribution for the sodium stearate grade 1 and sodium stearate grade 2, respectively. The percentages of fatty acids set forth above and below are based upon the total percentage of fatty acids in each respective sodium stearate grade, and is not based upon the total weight of the stick composition.

TABLE A

Preferred fatty acid distribution for sodium stearate grade 1

| Chain Length of Fatty Acid | Percentage |
|---|---|
| C12:0* and lower | 3.0 max |
| C14:0 | 3.0 max |
| C14:1** & C15:0 | 2.0 max |
| C16:0 | 20.0 to 30.0 |

TABLE A-continued

Preferred fatty acid distribution for sodium stearate grade 1

| Chain Length of Fatty Acid | Percentage |
| --- | --- |
| C16:1 and C17:0 | 2.0 max |
| C18:0 | 30.0 to 40.0 |
| C18:1 and C19:0 | 2.0 max |
| C20:0 | 15.0 to 18.0 |
| C22:0 | 15.0 to 20.0 |
| Greater than C22:0 | 3.0 max |

TABLE B

Preferred fatty acid distribution for sodium stearate grade 2

| Chain Length of Fatty Acid | Percentage |
| --- | --- |
| C12:0* and lower | 2.0 max |
| C14:0 | 6.0 max |
| C14:1** & C15:0 | 2.0 max |
| C16:0 | 50.0 to 70.0 |
| C16:1 and C17:0 | 3.0 max |
| C18:0 | 38.0 to 46.0 |
| Greater than C18:0 | 2.0 max |

*":0" denotes a saturated fatty acid.
**":1" denotes a fatty acid having 1 double bond.

The present invention also includes a plasticizer. Related U.S. patent application Ser. No. 08/949,219 (which is incorporated in its entirety herein by reference), which is owned by the assignee of the present invention, disclosed that the addition of certain plasticizers provided clear or translucent deodorant stick compositions that avoided the limitations of the prior art. Plasticizers disclosed in the aforementioned application, such as polyoxyethylene-polyoxypropylene 2-decyltetradecyl ethers and ethoxylated dimethicone copolyols, are also useful in the present invention.

In plasticizers having an ethylene oxide, it is believed that the moles of ethylene oxide component can range from about 4 moles to about 50 moles. Examples of more preferred plasticizers for practicing the present invention are the NIKKOL PEN series of solubilizers sold by Nikko Chemicals Co., Ltd. The PEN series includes various polyoxyethylene-polyoxypropylene 2-decyltetradecyl ethers, such as POE(12)POP(6) 2-decyltetradecyl ether, POE(20)POP(6) 2-decyltetradecyl ether, and POE(30)POP(6) 2-decyltetradecyl ether, which are sold as NIKKOL PEN-4612, PEN-4620, PEN-4630 respectively. The CTFA adopted names for these compounds are PPG-6-decyltetradeceth-12, PPG-6-decyltetradeceth-20, and PPG-6-decyltetradeceth-30 respectively. The most preferred plasticizer is PEG-15-PPG-6-Isotetracosanyl ether. A non-limiting example of the foregoing most preferred plasticizer is available from Heterene Inc. under the tradename Hetoxol I 24-EP-15-6.

The plasticizer is preferably present at about 1 wt % to about 10 wt %, more preferably at about 1.5 wt % to about 6 wt %, with about 3 wt % to about 5 wt % being most preferred. Table C below sets forth the preferred plasticizers/solubilizers and their preferred ranges.

TABLE C

| | Preferred Range (wt %) | Most Preferred (wt %) |
| --- | --- | --- |
| PPG-6-decyltetradeceth-12 | 2.5–6 | 4.5 |
| PPG-6-decyltetradeceth-20 | 2.5–5.5 | 3.5 |
| PPG-6-decyltetradeceth-30 | 1.5–4.5 | 3.0 |
| PEG-15-PPG-6-Isotetracosanyl ether | 2.5–5 | 4.5 |

Other plasticizers are also preferred for use in the stick compositions of the present invention. These plasticizers may be used in place of, or in addition to, the preferred PEN series. Of these, the preferred plasticizer is an ethoxylated dimethicone copolyol. It is preferred that the ethoxylated dimethicone copolyol be present at about 2 to about 6 wt %, with about 3.5 wt % to about 4 wt % being more preferred. Most preferred for use in the stick compositions of the present invention is Silicone Fluid SF1288, CTFA name Dimethicone Copolyol, available commercially from GE Silicones.

The clarity/stability enhancing agent provides the improved clear stick composition of the present invention, with improved initial clarity/transparency, and also enhances the high temperature stability of the stick composition. Also, syneresis is decreased even when sticks are stored at 110° F. for a month. The clarity/stability enhancing agent also improves the initial appearance and stability of stick compositions having PEN solubilizers.

The clarity/stability enhancing agent is a PPG $C_3$ to $C_8$ polyol. The stick composition of the present invention has from 3 wt % to about 10 wt %, more preferably 5 wt %, of the PPG $C_3$ to $C_8$ polyol. The PPG $C_3$ to $C_8$ polyol component is most preferably polyoxypropylene (10) butanediol (hereinafter "PPG-10 butanediol"). A non-limiting example of a PPG-10 butanediol that may be used in the present invention is available from Croda, Inc. under the tradename Probutyl DB-10.

Although it is preferred that the PPG $C_3$ to $C_8$ polyol has a butanediol component, the length of the carbon chain can be increased up to $C_8$ if there is a corresponding increase in hydroxyl groups. The corresponding increase in hydroxyl groups is required to maintain solubility of the PPG $C_3$ to $C_8$ polyol. A non-limiting example of such a contemplated PPG $C_3$ to $C_8$ polyol is PPG 10 hexahydric octanol. In addition, it is also believed that the mole percentage of PPG can also be increased if accompanied by a proportional increase in hydroxyl groups in order to maintain solubility.

The stick compositions of the present invention may include adjunct ingredients such as deodorants, antiperspirants, emollients, colorants, glitter agents, pigmented/colored particles, medicinal agents, fragrances and cooling agents or rubifacients/warming agents. Because of the improved clarity of the stick composition, the visibility of incorporated glitter agents and/or colored particles through the stick composition will be enhanced, thus, providing a more pleasing overall appearance. Examples of such glitter agents include coated/treated polyethylene terephthalate and titanium dioxide coated mica. A non-limiting example of such a coated/treated polyethylene terephthalate is available from Glitterex Corp. under the tradename 0.008" square Dark Gold poly*flake. A non-limiting example of such a titanium dioxide coated mica is available from Presperse Inc. under the tradename Flonac ME 10 C. In the alternative, opacifying agents can also be added if a clear or translucent product is not desired.

One example of a preferred stick composition of the present invention is a clear stick deodorant. In U.S. patent application Ser. No. 08/949,219, it was disclosed that the addition of PPG-10 butanediol enhanced the high temperature stability of clear stick deodorants having ethoxylated dimethicone copolyol plasticizers when stored at 110° F. for a month. However, it is believed that the addition of the clarity/stability enhancing agent of the present invention will enhance the stability of clear stick deodorant having other plasticizers, such as those disclosed herein. In fact, it has been found that PPG-10 butanediol provides better stability with respect to clarity in a clear stick deodorant composition than either Amidox C-5 or Procetyl-10. (Amidox C-5 is the tradename of an alkoxylated alkanol amide available from Stepan, Inc. Procetyl-10 is a tradename of a PPG-10 cetyl ether available from Croda, Inc.)

When the present invention is a clear stick deodorant, the clear stick composition further includes an odor-controlling agent. The odor-controlling agent is preferably a germicidal agent, a deodorizing agent, a masking agent, or a mixture thereof.

It is more preferred that the clear stick deodorants of the present invention include a germicidal agent. Of the commercially available germicidal agents suitable for use in underarm deodorants, the most preferred is a trichlorohydroxy diphenyl ether (CTFA name Triclosan). A non-limiting example of such a trichlorohydroxy diphenyl ether is available from Ciba Specialty Chemicals Corp under the tradename Irgasan DP-300. The germicidal agent is preferably present at less than about 2 wt %.

It is preferred that such clear stick deodorants also include a fragrance or other deodorizing or masking agent. Most commercially available fragrances are suitable for use in the clear stick deodorants of the present invention. Preferably, the fragrance is present at less than about 2 wt %.

The following are examples of two clear stick compositions according to the present invention.

| Ingredient | Weight Percent (wt %) |
| --- | --- |
| Example 1 A clear stick deodorant composition. | |
| Propylene glycol-solvent | 69.185 |
| Demineralized water-solvent | 15.00 |
| Sodium stearate-geliant | 6.00 |
| Dimethicone copolyol-ws-ethoxyiated -solubilizer/plasticizer | 3.50 |
| Trichlorohydroxy diphenyl ether-germicide | 0.30 |
| PPG-10 butanediol-clarity/ stability enhahcing agent | 5.00 |
| Fragrance | 1.00 |
| FD&C dyes | 0.015 |
| Example 2 A contemplated clear stick composition. | |
| Propylene glycol-solvent | 69.485 |
| Demineralized water-solvent | 15.00 |
| Sodium stearate-gellant | 6.00 |
| PPG-6-decyltetradeceth-20 -solubilizer/plasticizer | 3.50 |
| PPG-10 butanediol -clarity/stability enhancing agent | 5.00 |
| Fragrance | 1.00 |
| FD&C dyes | 0.015 |

It must be emphasized that the clear stick composition of the present invention is useful for delivering a variety of components, such as fragrances, cooling agents, pigmented particles, glittering agents, rubifacients and medicinal agents.

The present invention provides a stick composition that is substantially transparent or translucent and that has a smooth, silky feel on contact with the skin.

The invention having been thus described with particular reference to the preferred forms thereof, it will be obvious that various changes and modifications may be made therein without departing from the spirit and scope of the invention as defined in the appended claims.

What is claimed is:

1. A clear stick composition comprising:
    a solvent;
    a gelling agent;
    a plasticizer; and
    a PPG $C_3$ to $C_8$ polyol.
2. The clear stick composition of claim 1, wherein said PPG $C_3$ to $C_8$ polyol is polyoxypropylene (10) butanediol.
3. The clear stick composition of claim 1, wherein said solvent is selected from the group consisting of a $C_2$ to $C_6$ polyhydric alcohol, water, and mixtures thereof.
4. The clear stick composition of claim 1, wherein said solvent is a mixture of water and propylene glycol.
5. The clear deodorant stick composition of claim 1, wherein said solvent is present at about 70 to about 95 wt %.
6. The clear deodorant stick composition of claim 1, wherein said gelling agent is a soap-type agent.
7. The clear stick composition of claim 6, wherein said gelling agent is a mixture of two or more fatty acid salts.
8. The clear stick composition of claim 7, wherein said mixture includes sodium stearate.
9. The clear stick composition of claim 1, wherein said gelling agent is present at about 4 to about 10 wt %.
10. The clear stick composition of claim 1, wherein said plasticizer is selected from the group consisting of a polyoxyethylene-polyoxypropylene 2-decyltetradecyl ether, an ethoxylated dimethicone copolyol, and mixtures thereof.
11. The clear deodorant stick composition of claim 1, wherein said plasticizer is selected from the group consisting of POE(12)POP(6) 2-decyltetradecyl ether, POE(20)POP(6) 2-decyltetradecyl ether, POE(30)POP(6) 2-decyltetradecyl ether, PEG-15-PPG 6 isotetracosanyl ether, and mixtures thereof.
12. The clear stick composition of claim 1, wherein said plasticizer is PEG-15-PPG 6 isotetracosanyl ether.
13. The clear stick composition of claim 1, further comprising a glitter agent.
14. The clear stick composition of claim 13, wherein said glitter agent is selected from the group consisting of coated/treated polyethylene terephthalate, titanium dioxide coated mica, and mixtures thereof.
15. The clear stick composition of claim 1, further comprising an odor controlling agent selected from the group consisting of a germicidal agent, a deodorizing agent, a masking agent, and mixtures thereof.
16. The clear stick composition of claim 15, wherein said odor-controlling agent is selected from the group consisting of trichlorohydroxy diphenyl ether, cetyl trimethyl ammonium chloride, cetyl trimethyl ammonium bromide, and mixtures thereof.
17. The clear stick composition of claim 15, wherein said odor-controlling agent is trichlorohydroxy diphenyl ether.
18. A clear stick composition comprising:
    from about 70 wt % to about 95 wt % of a solvent;
    from about 4 wt % to about 10 wt % of a gelling agent;
    from about 1 wt % to about 10 wt % of a plasticizer; and
    from about 3 wt % to about 10 wt % of a PPG $C_3$ to $C_8$ polyol.

19. A method of deodorizing skin or reducing perspiration comprising the step of topically applying the clear stick composition of claim 1, wherein the clear stick composition further comprises an ingredient selected from the group consisting of deodorants, antiperspirants and mixtures thereof.

20. A method of enhancing the clarity or stability of a clear stick composition, the method comprising the steps of:
    adding a PPG $C_3$ to $C_8$ polyol to a mixture, and
    forming the clear stick composition from said mixture.

\* \* \* \* \*